United States Patent
Lee et al.

(10) Patent No.: US 11,515,729 B2
(45) Date of Patent: Nov. 29, 2022

(54) APPARATUS AND METHOD WITH WIRELESS POWER RELAY

(71) Applicant: SAMSUNG ELECTRONICS CO., LTD., Gyeonggi-do (KR)

(72) Inventors: Hankyu Lee, Suwon-si (KR); Sang Joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 17/181,393

(22) Filed: Feb. 22, 2021

(65) Prior Publication Data

US 2022/0077717 A1 Mar. 10, 2022

(30) Foreign Application Priority Data

Sep. 9, 2020 (KR) .................. 10-2020-0115405

(51) Int. Cl.
*H02J 50/12* (2016.01)
*H02J 7/34* (2006.01)
*A61N 1/378* (2006.01)

(52) U.S. Cl.
CPC .............. *H02J 50/12* (2016.02); *H02J 7/345* (2013.01); *A61N 1/3787* (2013.01)

(58) Field of Classification Search
CPC .......... H02J 50/12; H02J 7/345; A61N 1/3787
See application file for complete search history.

(56) References Cited

U.S. PATENT DOCUMENTS

| | | | | |
|---|---|---|---|---|
| 3,745,382 A * | 7/1973 | Hoge | ................... | H03K 17/292 327/402 |
| 3,961,473 A * | 6/1976 | Hung | ..................... | G04G 15/00 368/110 |
| 5,919,216 A | 7/1999 | Houben et al. | | |
| 6,049,178 A * | 4/2000 | Sheu | ....................... | H02J 9/065 307/64 |

(Continued)

FOREIGN PATENT DOCUMENTS

| EP | 2 512 001 A2 | 10/2012 |
|---|---|---|
| EP | 2 922 175 A1 | 9/2015 |

(Continued)

OTHER PUBLICATIONS

Extended European Search Report dated Jan. 4, 2022 in counterpart European Patent Application No. 21185030.0 (8 pages in English).

*Primary Examiner* — Daniel Kessie
*Assistant Examiner* — Brian K Baxter
(74) *Attorney, Agent, or Firm* — NSIP Law

(57) ABSTRACT

A wireless power relay apparatus includes: a first antenna configured to wirelessly receive an alternating current (AC) power signal of a first frequency from a wireless power transmission apparatus; a rectifier configured to convert the received AC power signal into a direct current (DC) power; a storage device configured to store electric energy of the DC power output from the rectifier; a power oscillator configured to generate an AC power signal of a second frequency based on an output current of the rectifier and electric energy of a DC voltage stored in the storage device; and a second antenna configured to transmit the AC power signal of the second frequency to a wireless power reception apparatus.

20 Claims, 9 Drawing Sheets

(56) References Cited

U.S. PATENT DOCUMENTS

| | | |
|---|---|---|
| 7,379,775 B2 | 5/2008 | Parramon et al. |
| 7,417,482 B2 | 8/2008 | Elgebaly et al. |
| 8,983,621 B2 | 3/2015 | Hou et al. |
| 9,083,424 B2 | 7/2015 | Otis et al. |
| 9,386,934 B2 | 7/2016 | Parker et al. |
| 9,559,605 B2 | 1/2017 | Gudan et al. |
| 10,680,636 B2 | 6/2020 | Kim et al. |
| 2001/0015634 A1* | 8/2001 | Shirakawa ............ H02J 7/0022 320/110 |
| 2011/0115430 A1* | 5/2011 | Saunamaki ............ H02J 7/025 320/108 |
| 2013/0002191 A1* | 1/2013 | Jung ................. H02J 50/10 320/103 |
| 2013/0079849 A1* | 3/2013 | Perryman .......... A61N 1/37229 607/60 |
| 2015/0130409 A1* | 5/2015 | Lee ................. H02J 50/70 320/108 |
| 2015/0229134 A1 | 8/2015 | Masaoka et al. |
| 2015/0380972 A1 | 12/2015 | Fort |
| 2016/0181822 A1 | 6/2016 | Yang et al. |
| 2016/0263385 A1* | 9/2016 | Aghassian ............ A61N 1/3787 |
| 2016/0276861 A1* | 9/2016 | Tages ................. H02J 50/12 |
| 2017/0207656 A1* | 7/2017 | Boys ................. H02J 50/10 |
| 2017/0207824 A1 | 7/2017 | Von Novak, III et al. |
| 2017/0264141 A1* | 9/2017 | Von Novak, III ...... H02J 50/50 |
| 2017/0271919 A1 | 9/2017 | Von Novak, III et al. |
| 2018/0062515 A1 | 3/2018 | Jung |
| 2018/0133471 A1 | 5/2018 | Lee et al. |
| 2018/0219420 A1 | 8/2018 | Xu et al. |
| 2020/0136676 A1 | 4/2020 | Yun et al. |
| 2020/0144847 A1 | 5/2020 | Fang et al. |
| 2020/0366133 A1 | 11/2020 | Lee et al. |
| 2022/0149720 A1* | 5/2022 | Coles ................. H02M 1/0009 |

FOREIGN PATENT DOCUMENTS

| | | |
|---|---|---|
| KR | 10-1880781 B1 | 7/2018 |
| KR | 10-2019-0002475 A | 1/2019 |
| KR | 10-2019-0035753 A | 4/2019 |
| KR | 10-2023617 B1 | 9/2019 |

\* cited by examiner

APPARATUS AND METHOD WITH WIRELESS POWER RELAY

CROSS-REFERENCE TO RELATED APPLICATIONS

This application claims the benefit under 35 USC § 119(a) of Korean Patent Application No. 10-2020-0115405, filed on Sep. 9, 2020, in the Korean Intellectual Property Office, the entire disclosure of which is incorporated herein by reference for all purposes.

BACKGROUND

1. Field

The following description relates to an apparatus and method with wireless power relay.

2. Description of Related Art

Wireless power may refer to energy transmitted from a wireless power transmitter to a wireless power receiver via magnetic coupling. A wireless power charging system may include a wireless power transmitter configured to wirelessly transmit power, and a wireless power receiver configured to wirelessly receive power. The wireless power transmitter may include a source resonator, and the wireless power receiver may include a target resonator. Magnetic coupling or resonance coupling may occur between the source resonator and the target resonator, and power may be wirelessly transmitted from the wireless power transmitter to the wireless power receiver via the magnetic coupling or the resonance coupling.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a wireless power relay apparatus includes: a first antenna configured to wirelessly receive an alternating current (AC) power signal of a first frequency from a wireless power transmission apparatus; a rectifier configured to convert the received AC power signal into a direct current (DC) power; a storage device configured to store electric energy of the DC power output from the rectifier; a power oscillator configured to generate an AC power signal of a second frequency based on an output current of the rectifier and electric energy of a DC voltage stored in the storage device; and a second antenna configured to transmit the AC power signal of the second frequency to a wireless power reception apparatus.

The power oscillator may be configured to start to oscillate, in response to a reception of the AC power signal of the first frequency and the DC voltage stored in the storage device reaching a reference value.

The power oscillator may be configured to remain in an off state until the DC voltage reaches the reference value, start to oscillate at a point in time at which the DC voltage reaches the reference value, and generate the AC power signal of the second frequency, without being controlled by a control signal.

The power oscillator may be configured to oscillate at the second frequency based on the DC voltage supplied from the storage device and the current supplied from the rectifier.

The rectifier, the storage device, and the second antenna may be connected to a common node.

The storage device may be a capacitor, and an end of the capacitor may be connected to a ground terminal, and another end of the capacitor may be connected to the rectifier and the second antenna.

The wireless power relay apparatus may be configured to be detachably mounted on a surface of the wireless power transmission apparatus.

The first antenna may be configured to wirelessly receive the AC power signal of the first frequency from the wireless power transmission apparatus when the wireless power relay apparatus is detachably mounted on the surface of the wireless power transmission apparatus.

The wireless power transmission apparatus may be a mobile electronic device, and the AC power signal of the first frequency may be generated from electric energy stored in a battery of the mobile electronic device.

The wireless power reception apparatus may be an implantable apparatus or a body attachment apparatus.

The second frequency may be different from the first frequency, and the second frequency may be equal to an operating frequency for a wireless power reception of the wireless power reception apparatus.

The rectifier may include a plurality of diodes, and the power oscillator may include two transistors and a capacitor connected to an end of each of the two transistors.

The apparatus may include: a circuit board in which the rectifier and the power oscillator are disposed; a first insulating layer disposed between the first antenna and the circuit board; and a second insulating layer disposed between the circuit board and the second antenna.

A wireless power transmission system may include: the wireless power relay apparatus; and the wireless power transmission apparatus.

In another general aspect, a wireless power transmission system includes: a wireless power transmission apparatus configured to wirelessly transmit an alternating current (AC) power signal of a first frequency; and a wireless power relay apparatus configured to receive the AC power signal of the first frequency, convert the received AC power signal into a direct current (DC) power, generate an AC power signal of a second frequency based on the DC power, and transmit the generated AC power signal of the second frequency to a wireless power reception apparatus.

The wireless power relay apparatus may include: a rectifier configured to convert the received AC power signal into the DC power; a storage device configured to store electric energy of the DC power output from the rectifier; and a power oscillator configured to generate the AC power signal of the second frequency based on an output current of the rectifier and electric energy of a DC voltage stored in the storage device.

The wireless power relay apparatus may be configured to be detachably mounted on a surface of the wireless power transmission apparatus.

The wireless power transmission apparatus may be a mobile electronic device, and the wireless power reception apparatus may be an implantable apparatus or a body attachment apparatus.

In another general aspect, a wireless power relay method includes: wirelessly receiving, using a first antenna, an alternating current (AC) power signal of a first frequency from a wireless power transmission apparatus; converting, using a rectifier, the received AC power signal into a direct current (DC) power; storing, in a storage device, electric energy of the DC power output from the rectifier; generating, using a power oscillator, an AC power signal of a second frequency based on an output current of the rectifier and electric energy of a DC voltage stored in the storage device; and transmitting, using a second antenna, the AC power signal of the second frequency to a wireless power reception apparatus.

The generating of the AC power signal of the second frequency may include the power oscillator starting to oscillate, in response to a reception of the AC power signal of the first frequency and the DC voltage reaching a reference value.

The wireless power transmission apparatus may be a mobile electronic device, the AC power signal of the first frequency may be generated from electric energy stored in a battery of the mobile electronic device, and the wireless power reception apparatus may be an implantable apparatus or a body attachment apparatus.

The second frequency may be different from the first frequency and may be identical to an operating frequency for a wireless power reception of the wireless power reception apparatus.

Other features and aspects will be apparent from the following detailed description, the drawings, and the claims.

Figure 1:
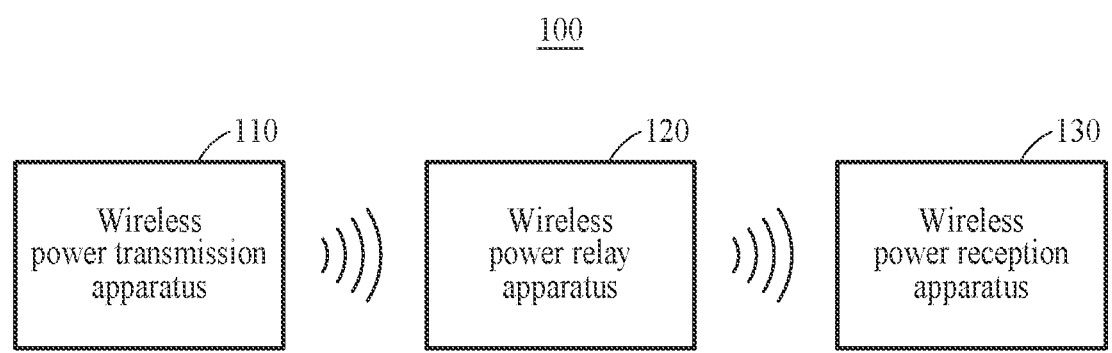
FIG. 1 illustrates an example of a wireless power transmission system.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art, after an understanding of the disclosure of this application, may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The following structural or functional descriptions of examples disclosed in the present disclosure are merely intended for the purpose of describing the examples and the examples may be implemented in various forms. The examples are not meant to be limited, but it is intended that various modifications, equivalents, and alternatives are also covered within the scope of the claims.

Although terms of "first" or "second" are used to explain various members, components, regions, layers, or sections, the members, components, regions, layers, or sections are not limited to the terms. These terms should be used only to distinguish one member, component region, layer, or section from another member, component region, layer, or section. Thus, a first member, component, region, layer, or section referred to in examples described herein may also be referred to as a second member, component, region, layer, or section without departing from the teachings of the examples.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. Likewise, expressions, for example, "between" and "immediately between" and "adjacent to" and "immediately adjacent to" may also be construed as described in the foregoing.

The terminology used herein is for the purpose of describing particular examples only and is not to be limiting of the present disclosure. As used herein, the singular forms "a", "an", and "the" are intended to include the plural forms as well, unless the context clearly indicates otherwise. As used herein, the term "and/or" includes any one and any combination of any two or more of the associated listed items. As used herein, the terms "include," "comprise," and "have" specify the presence of stated features, integers, steps, operations, elements, components, numbers, and/or combinations thereof, but do not preclude the presence or addition of one or more other features, integers, steps, operations, elements, components, numbers, and/or combinations thereof. The use of the term "may" herein with respect to an example or embodiment (for example, as to what an example or embodiment may include or implement) means that at least one example or embodiment exists where such a feature is included or implemented, while all examples are not limited thereto.

Unless otherwise defined herein, all terms used herein including technical or scientific terms have the same meanings as those generally understood. Terms defined in dictionaries generally used should be construed to have meanings matching with contextual meanings in the related art and the present disclosure, and are not to be construed as an ideal or excessively formal meaning unless otherwise defined herein.

Hereinafter, examples will be described in detail with reference to the accompanying drawings, and like reference numerals in the drawings refer to like elements throughout.

FIG. 1 illustrates an example of a wireless power transmission system (for example, a wireless power transmission system 100).

Referring to FIG. 1, the wireless power transmission system 100 may be a system configured to wirelessly transmit power of a wireless power transmission apparatus 110 to a wireless power reception apparatus 130. The wireless power transmission system 100 may include a wireless power relay apparatus 120 configured to relay power between the wireless power transmission apparatus 110 and the wireless power reception apparatus 130, in addition to the wireless power transmission apparatus 110 and the wireless power reception apparatus 130. In an example, the wireless power transmission system 100 may be a system in which the wireless power transmission apparatus 110 located outside a body wirelessly transmits power to the wireless power reception apparatus 130 that is located in the body or attached to the body, through the wireless power relay apparatus 120.

The wireless power transmission apparatus 110 may be an apparatus configured to wirelessly transmit power. The wireless power transmission apparatus 110 may be or include, for example, a smartphone, a tablet, a mobile phone, a netbook, an electronic notebook, a wearable device, and/or a wireless power charger. In an example, the wireless power transmission apparatus 110 may wirelessly transmit an alternating current (AC) power signal of a first frequency using a near field communication (NFC).

The wireless power relay apparatus 120 may be an apparatus configured to relay power received from the wireless power transmission apparatus 110 to the wireless power reception apparatus 130. In an example, the wireless power relay apparatus 120 may receive an AC power signal of a first frequency from the wireless power transmission apparatus 110, and may convert the received AC power signal into a direct current (DC) power. The wireless power relay apparatus 120 may generate an AC power signal of a second frequency based on the DC power, and may transmit the generated AC power signal of the second frequency to the wireless power reception apparatus 130. In this example, the second frequency may be different from the first frequency.

The wireless power reception apparatus 130 may be an apparatus configured to wirelessly receive power and to perform a predetermined function based on the received power, and may be or include, for example, an implantable apparatus or a body attachment apparatus. For example, the wireless power reception apparatus 130 may be a medical device that is inserted into a body or attached to the body and configured to sense biometric information or provide biostimulation for treatment. However, a type of the wireless power reception apparatus 130 is not limited to the medical device, and all apparatuses capable of wirelessly receiving power may be used without a limitation. The wireless power reception apparatus 130 may be, for example, a sensor, or an Internet of Things (IoT) apparatus.

In an example, when the wireless power reception apparatus 130 is an implantable apparatus, power may need to be wirelessly transmitted from an external device to a device inserted into a body. In this example, a unique optimized wireless power transmission frequency is often used in consideration of a rate of power transfer to a body and a size of a receiver of the wireless power reception apparatus 130. In general, when a wireless power transmission frequency decreases, the rate of power transfer to the body and the size of the receiver may tend to increase. Also, an optimal wireless power transmission frequency for the implantable apparatus may be set based on power used for charging, an allowable size of the receiver, and/or a depth of insertion of the wireless power reception apparatus 130 into the body.

When a wireless power transmission frequency of the wireless power transmission apparatus 110 is fixed (as may typically be the case), the wireless power transmission frequency of the wireless power transmission apparatus 110 may not match an optimal wireless power transmission frequency for the wireless power reception apparatus 130. In this example, it may be difficult to achieve an optimal efficiency of a wireless power transmission. In this example, the wireless power reception apparatus 130 may need to use a dedicated charger for the optimal wireless power transmission frequency, which may lead to a reduction in a user's convenience because the dedicated charger needs to be carried and managed.

In contrast, the wireless power relay apparatus 120 of one or more embodiments may convert wireless power of a first frequency received from the wireless power transmission apparatus 110 into wireless power of a second frequency, and may transmit the wireless power of the second frequency to the wireless power reception apparatus 130, and thus the wireless power relay apparatus 120 of one or more embodiments may prevent a decrease in a power conversion efficiency due to a difference in characteristics of wireless power transmission frequencies between the wireless power transmission apparatus 110 and the wireless power reception apparatus 130. Also, the wireless power relay apparatus 120 may be implemented in a form of an accessory, and thus may be easily carried and may wireless transmit power even without a dedicated charger for the wireless power reception apparatus 130, thereby enhancing user convenience.

Figure 2A:
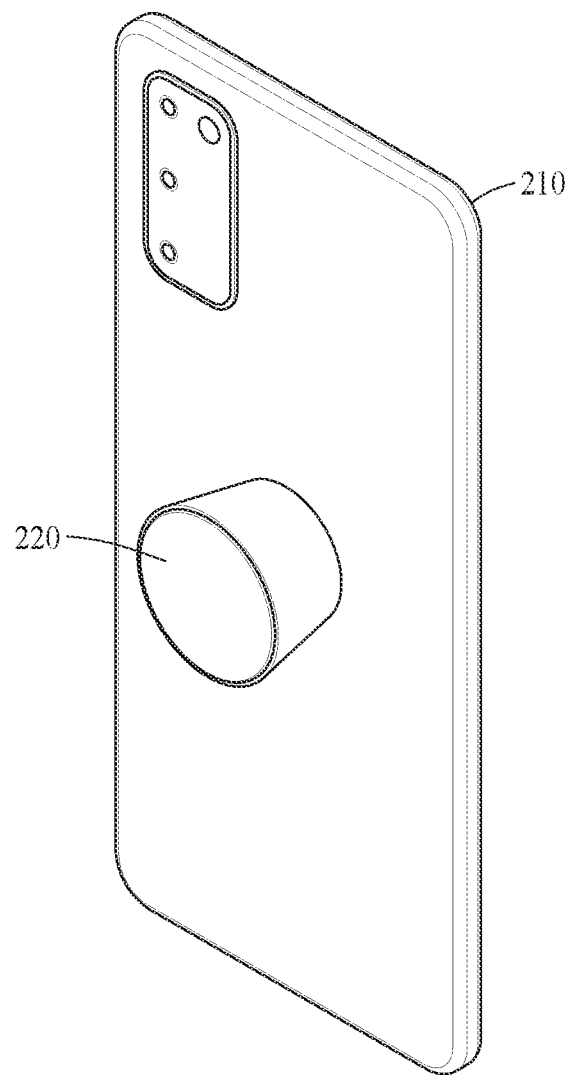
FIGS. 2A and 2B illustrate examples of a wireless power relay apparatus.
Figure 2B:
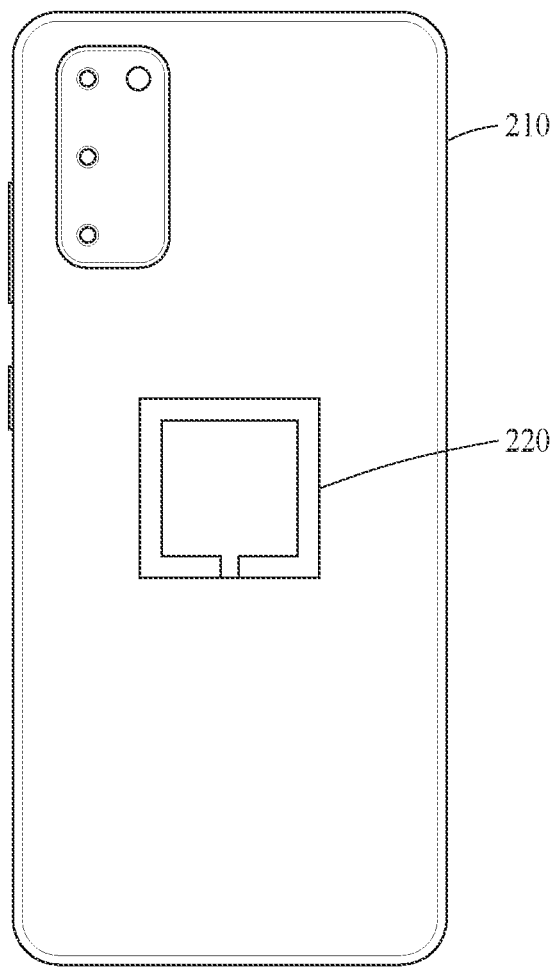

FIGS. 2A and 2B illustrate examples of a wireless power relay apparatus (for example, a wireless power relay apparatus 220).

Referring to FIGS. 2A and 2B, a wireless power transmission apparatus 210 may be a mobile electronic device (for example, a smartphone). A widely used apparatus such as a smartphone may operate as the wireless power transmission apparatus 210, and the wireless power transmission apparatus 210 may generate an AC power signal of a first frequency for a wireless power transmission, and may transmit the AC power signal via an antenna of the wireless power transmission apparatus 210 to the outside of the wireless power transmission apparatus 210.

In an example, the wireless power relay apparatus 220 may be detachably implemented on one surface of the wireless power transmission apparatus 210. For example, in FIGS. 2A and 2B, the wireless power relay apparatus 220 may be attached to a rear side of the wireless power transmission apparatus 210 and may operate. The wireless power relay apparatus 220 may be implemented in the form of a portable accessary, for example, a coin, a card, a card holder, and/or a collapsible grip, however, the implementation form is not limited. In order to supply power to a wireless power reception apparatus, a user carrying the wireless power transmission apparatus 210 may only need to additionally carry the wireless power relay apparatus 220 of one or more embodiments in the form of an accessory for a wireless power relay, and thus portability may be enhanced and user convenience may increase.

Figure 3:
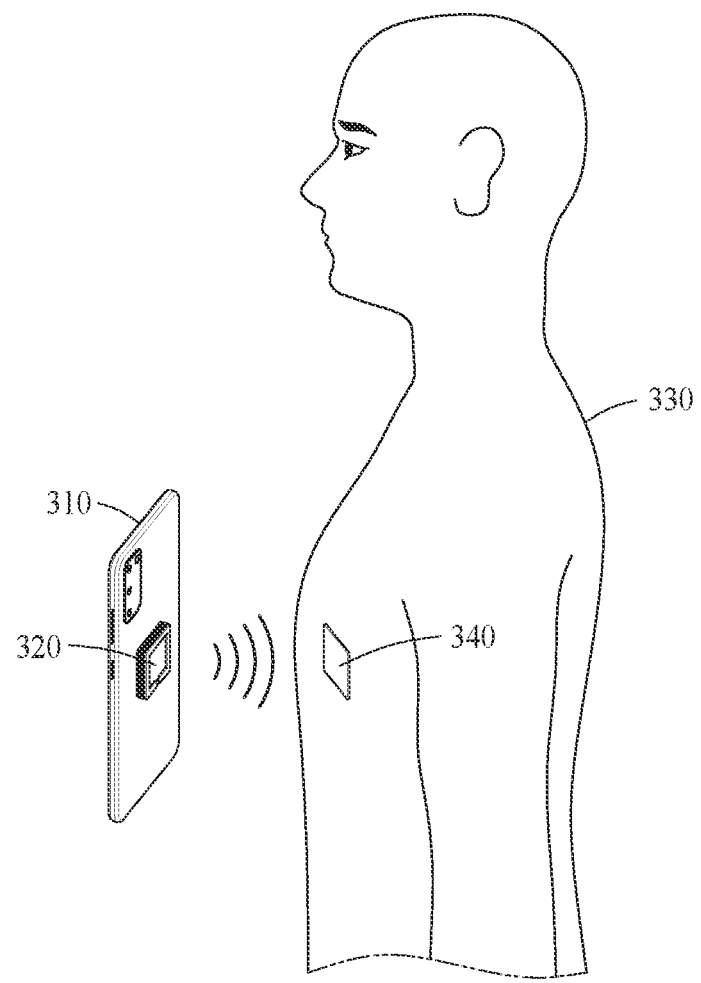
FIG. 3 illustrates an example of an operation of a wireless power relay apparatus.

FIG. 3 illustrates an example of an operation of a wireless power relay apparatus (for example, a wireless power relay apparatus 320).

Referring to FIG. 3, a wireless power transmission apparatus 310 (for example, a smartphone) may generate an AC power signal of a first frequency based on electric energy stored in an internal battery of the wireless power transmission apparatus 310 or an external battery, and may output the AC power signal of the first frequency to the outside. In an example, the wireless power relay apparatus 320 may receive the AC power signal of the first frequency from the wireless power transmission apparatus 310 via mutual coupling between coils (for example, between a coil of the wireless power transmission apparatus 310 and a coil of the wireless power relay apparatus 320), may convert the received AC power signal of the first frequency into an AC power signal of a second frequency, and may transmit the AC power signal of the second frequency to a wireless power reception apparatus 340.

In an example, the wireless power reception apparatus 340 may be a medical apparatus inserted into a body of a user 330. In this example, the wireless power reception apparatus 340 may be, for example, an implantable medical apparatus, such as a deep brain neurostimulator configured to sense a biosignal in a body or output a stimulation signal, a pacemaker, a cochlear implant, an insulin pump, or a gastric stimulator. However, the wireless power reception apparatus 340 is not limited to the implantable medical apparatus, and may correspond to various electronic apparatuses capable of wirelessly receiving power.

In a wireless power transmission between the wireless power transmission apparatus 310 and the wireless power reception apparatus 340, operating frequencies may be different from each other. The wireless power relay apparatus 320 of one or more embodiments may enhance an efficiency of the wireless power transmission by reducing a difference between the operating frequencies through a frequency conversion.

The wireless power relay apparatus 320 of one or more embodiments may change a frequency of wireless power so that various types of wireless power transmission apparatuses 310 may operate as a charger of the wireless power reception apparatus 340 inserted into the body without using a dedicated charger separate from the wireless power transmission apparatus 310, as may be used by a typical wireless power relay apparatus. Since such various types of wireless power transmission apparatuses 310 may operate as a charger of the wireless power reception apparatus 340 when used with the wireless power relay apparatus 320 of one or more embodiments, user convenience may be enhanced. The wireless power relay apparatus 320 of one or more embodiments may provide a great advantage to a wireless power charging system that uses an optimal frequency different from a frequency that is widely used for wireless power charging due to constraints such as a size or a location of use and a difficulty in freely relacing a battery in an implantable medical apparatus.

Since the wireless power relay apparatus 320 uses the wireless power transmission apparatus 310 as a power source, the wireless power relay apparatus 320 of one or more embodiments may transmit power to the wireless power reception apparatus 340 without including a processor and a battery that a typical wireless power relay apparatus may use to communicate with a wireless power reception apparatus. Also, the wireless power relay apparatus 320 implemented in the form of an accessory may be attached to one surface of the wireless power transmission apparatus 310 to be easily used. The wireless power relay apparatus 320 of one or more embodiments may output an AC power signal of an optimal operating frequency used by the wireless power reception apparatus 340 and may efficiently perform wireless power charging, regardless of a wireless power transmission frequency used by the wireless power transmission apparatus 310.

Also, the wireless power relay apparatus 320 of one or more embodiments may reduce a loss caused by penetration of the body of the user 330, through a frequency optimization. Various types of mobile electronic apparatuses may be used as the wireless power transmission apparatus 310 without a need for a dedicated charger in addition to the wireless power transmission apparatus 310, and thus the user convenience may be enhanced.

Figure 4:
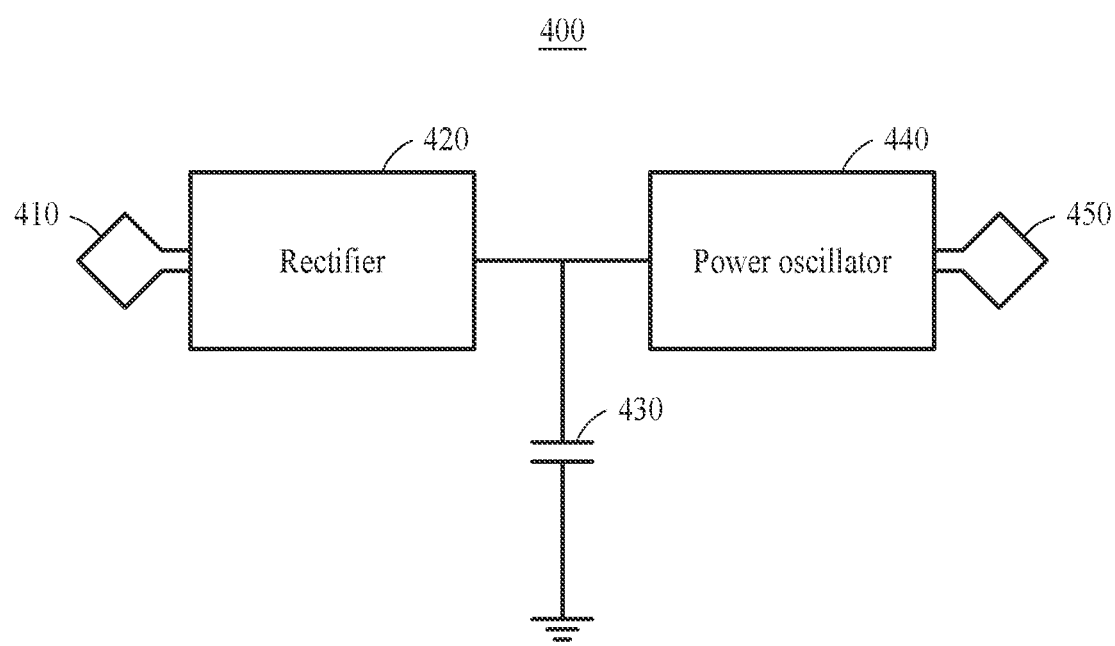
FIG. 4 illustrates an example of a configuration of a wireless power relay apparatus.

FIG. 4 illustrates an example of a configuration of a wireless power relay apparatus (for example, a wireless power relay apparatus 400).

Referring to FIG. 4, the wireless power relay apparatus 400 may include a first antenna 410, a rectifier 420, a storage device 430, a power oscillator 440, and a second antenna 450. In examples described herein, the term "antenna" may be referred to as a "coil".

The first antenna 410 may wirelessly receive power from a wireless power transmission apparatus. In a wireless power charging mode, the wireless power transmission apparatus may generate an AC power signal of a first frequency based on electric energy stored in a battery (for example, a battery included in the wireless power transmission apparatus), and may radiate the generated AC power signal of the first frequency to the outside. When the wireless power relay apparatus 400 is attached to or located near the wireless power transmission apparatus that is in the wireless power charging mode, the first antenna 410 may wirelessly receive the AC power signal of the first frequency from the wireless power transmission apparatus.

The rectifier 420 may convert the AC power signal of the first frequency received via the first antenna 410 into a DC power. The rectifier 420 may generate a DC voltage by rectifying the AC power signal, and may output the DC voltage. The rectifier 420 may be, for example, an active rectifier or a passive rectifier, and there is no limitation to a type of the rectifier 420.

The storage device 430 may store electric energy of the DC power output from the rectifier 420, and may be, for example, a capacitor. The storage device 430 may store the DC voltage output from the rectifier 420.

The power oscillator 440 may generate an AC power signal of a second frequency based on an output current of the rectifier 420 and electric energy of the DC voltage stored in the storage device 430. The second frequency may be different from the first frequency and may be identical to, or substantially similar to, an optimal operating frequency for a wireless power reception of a wireless power reception apparatus. The power oscillator 440 may oscillate at the second frequency based on the DC voltage supplied from the storage device 430 and a current supplied from the rectifier 420. The power oscillator 440 may have its own reference value for oscillation by a characteristic of a structure of an internal circuit thereof.

In an example, when a reception of the AC power signal of the first frequency occurs and when the DC voltage stored in the storage device 430 reaches the reference value, the power oscillator 440 may start to oscillate. For example, the power oscillator 440 may remain in an off state until the DC voltage reaches the reference value, may start to oscillate at a point in time at which the DC voltage reaches the reference value and may generate the AC power signal of the second frequency, without being controlled by a control signal.

The second antenna 450 may transmit the AC power signal of the second frequency generated by the power oscillator 440 to the wireless power reception apparatus.

As described above, the wireless power relay apparatus 400 may receive a wireless power signal of the first frequency from the wireless power transmission apparatus, may store the received wireless power signal in a form of an AC voltage in the storage device 430, may convert the wireless power signal into a wireless power signal of the second frequency, and may transmit the wireless power signal of the second frequency to the wireless power reception apparatus. The wireless power relay apparatus 400 of one or more embodiments may not require a separate battery to relay a wireless power transmission, and accordingly use of the wireless power relay apparatus 400 of one or more embodiments may reduce a size and a production cost, and increase a power conversion efficiency by minimizing a process of converting power.

Also, whether the power oscillator 440 is activated may be determined based on whether the wireless power relay apparatus 400 wirelessly receives power, and accordingly the power oscillator 440 may be activated without a separate configuration, for example, a processor, to control the power oscillator 440. In other words, the wireless power relay apparatus 400 of one or more embodiments may include active devices, instead of including a separate processor and a battery configured to operate the processor, and accordingly the wireless power relay apparatus 400 of one or more embodiments may be implemented as a compact accessory. Due to such a structure of the wireless power relay apparatus 400 of one or more embodiments, the wireless power relay apparatus 400 may relay a wireless power transmission, by changing a frequency for wireless power charging, instead of changing a structure of each of the wireless power transmission apparatus and the wireless power reception apparatus in an existing wireless power charging system.

The wireless power relay apparatus 400 may operate without being inserted into a body, and may easily change a frequency by changing the first antenna 410. Accordingly, any number of apparatuses (smartphones, wearable devices, etc., for example) may be used as a wireless power transmission apparatus.

Figure 5:
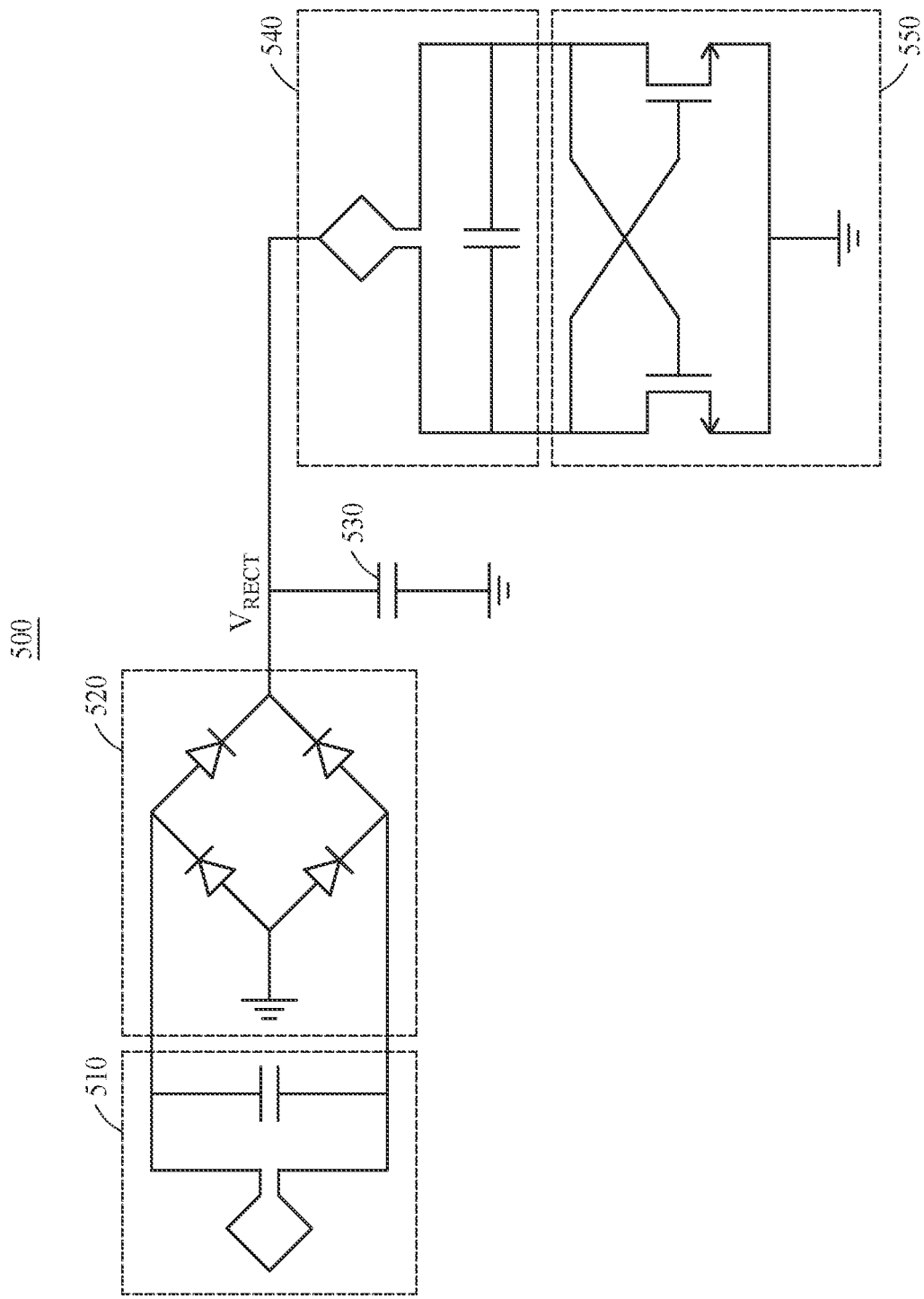
FIG. 5 illustrates an example of a circuit to implement a wireless power relay apparatus.

FIG. 5 illustrates an example of a circuit to implement a wireless power relay apparatus (for example, a wireless power relay apparatus 500).

Referring to the circuit of FIG. 5, the wireless power relay apparatus 500 may include a first antenna 510 configured to receive an AC power signal of a first frequency from a wireless power transmission apparatus, a rectifier 520 configured to convert the AC power signal of the first frequency received via the first antenna 510 into a DC power, a storage device 530 configured to store the DC power output from the rectifier 520 in a form of a DC voltage, a power oscillator 550 configured to oscillate at a second frequency based on a DC voltage stored in the storage device 530 and a current supplied from the rectifier 520 and to generate an AC power signal of the second frequency, and a second antenna 540 configured to transmit the AC power signal of the second frequency generated by the power oscillator 550.

The storage device 530 may be a capacitor, and one end of the capacitor may be connected to a ground terminal and another end of the capacitor may be connected to the rectifier 520 and the second antenna 540. The storage device 530 may store a DC voltage VRECT rectified by the rectifier 520. In an example, the rectifier 520 may include a plurality of diodes, and the power oscillator 550 may include two transistors and a capacitor that is connected to one end of each of the two transistors. In the circuit, the power oscillator 550 may be implemented without a separate control circuit, because the power oscillator 550 has its own reference value for the DC voltage VRECT supplied from the storage device 530.

The wireless power relay apparatus 500 may be implemented with a compact structure as shown in the circuit of FIG. 5, and thus the wireless power relay apparatus 500 of one or more embodiments may be manufactured with a small size and produce the wireless power relay apparatus 500 at a relatively low unit cost of production. Also, the wireless power relay apparatus 500 of one or more embodiments may enhance a power efficiency of a wireless power charging system through a frequency conversion of an AC power signal for wireless power charging. Even when it is difficult to change an operating frequency for wireless power charging of a wireless power reception apparatus, or when such operating frequency cannot be changed, the wireless power relay apparatus 500 may generate an AC power signal of a second frequency optimized for the wireless power charging of the wireless power reception apparatus, by changing the second antenna.

Figure 6:
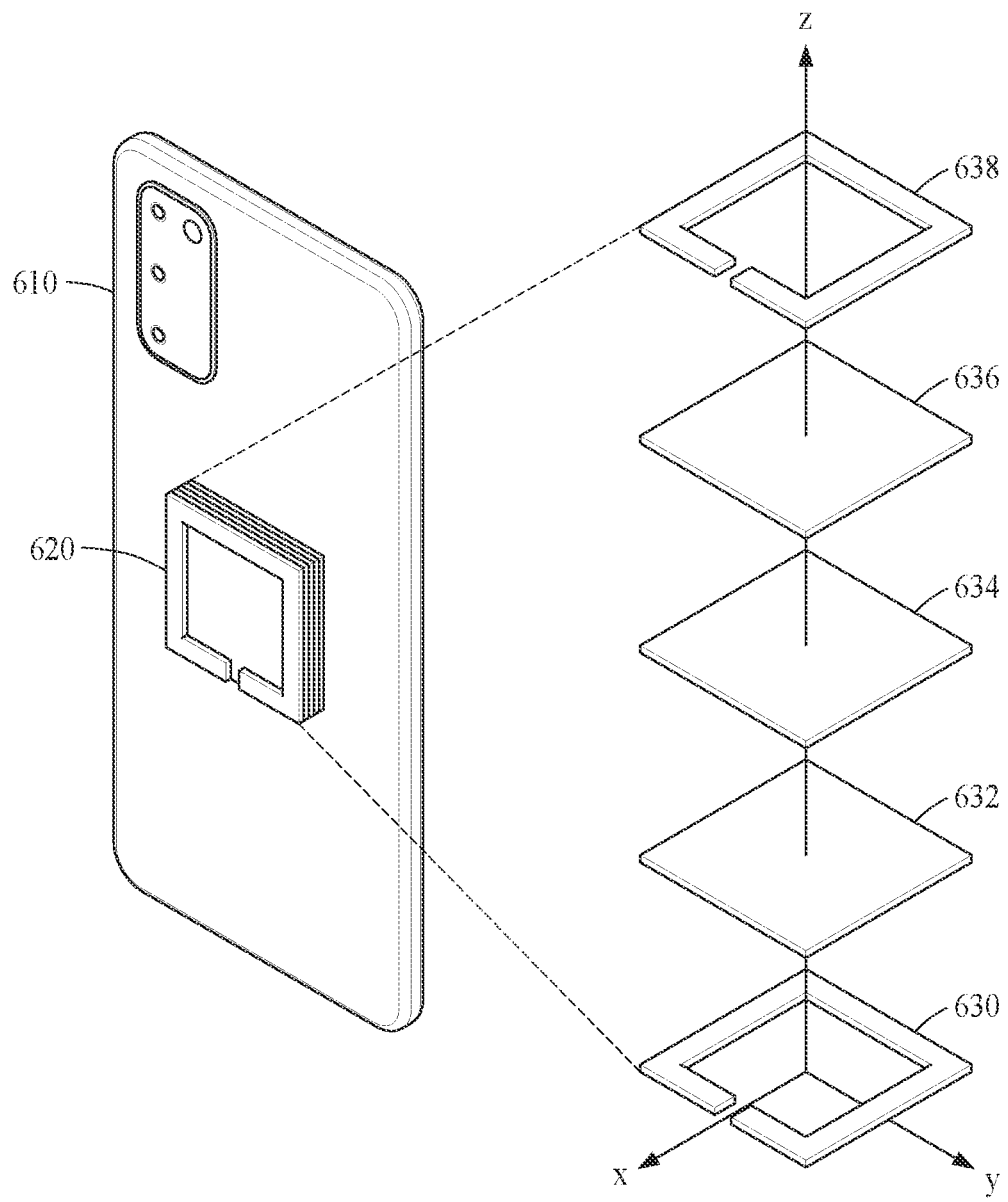
FIG. 6 illustrates an example of a structure of a wireless power relay apparatus.

FIG. 6 illustrates an example of a structure of a wireless power relay apparatus (for example, a wireless power relay apparatus 620).

Referring to FIG. 6, the wireless power relay apparatus 620 may be implemented in the form of an accessory disposed (for example, detachably mounted) on one surface of a wireless power transmission apparatus 610 (for example, a smartphone). The wireless power relay apparatus 620 may include a first antenna 630 configured to receive an AC power signal of a first frequency from the wireless power transmission apparatus 610, a circuit board 634 in which a rectifier and a power oscillator are disposed and/or included, a second antenna 638 configured to transmit an AC power signal of a second frequency generated by the power oscillator, a first insulating layer 632 disposed between the first antenna 630 and the circuit board 634, and a second insulating layer 636 disposed between the circuit board 634 and the second antenna 638. The first antenna 630 and the circuit board 634 may be connected to each other through a wiring, and the circuit board 634 and the second antenna 638 may be connected to each other through a wiring. In an example, the first antenna 630 is disposed closer to the one surface of the wireless power transmission apparatus 610 than the second antenna 638 when the wireless power relay apparatus 620 is disposed on the one surface.

Through the above structure, the wireless power relay apparatus 620 of one or more embodiments may be implemented with a relatively high power conversion efficiency by reducing a size and a unit cost of production.

Figure 7:
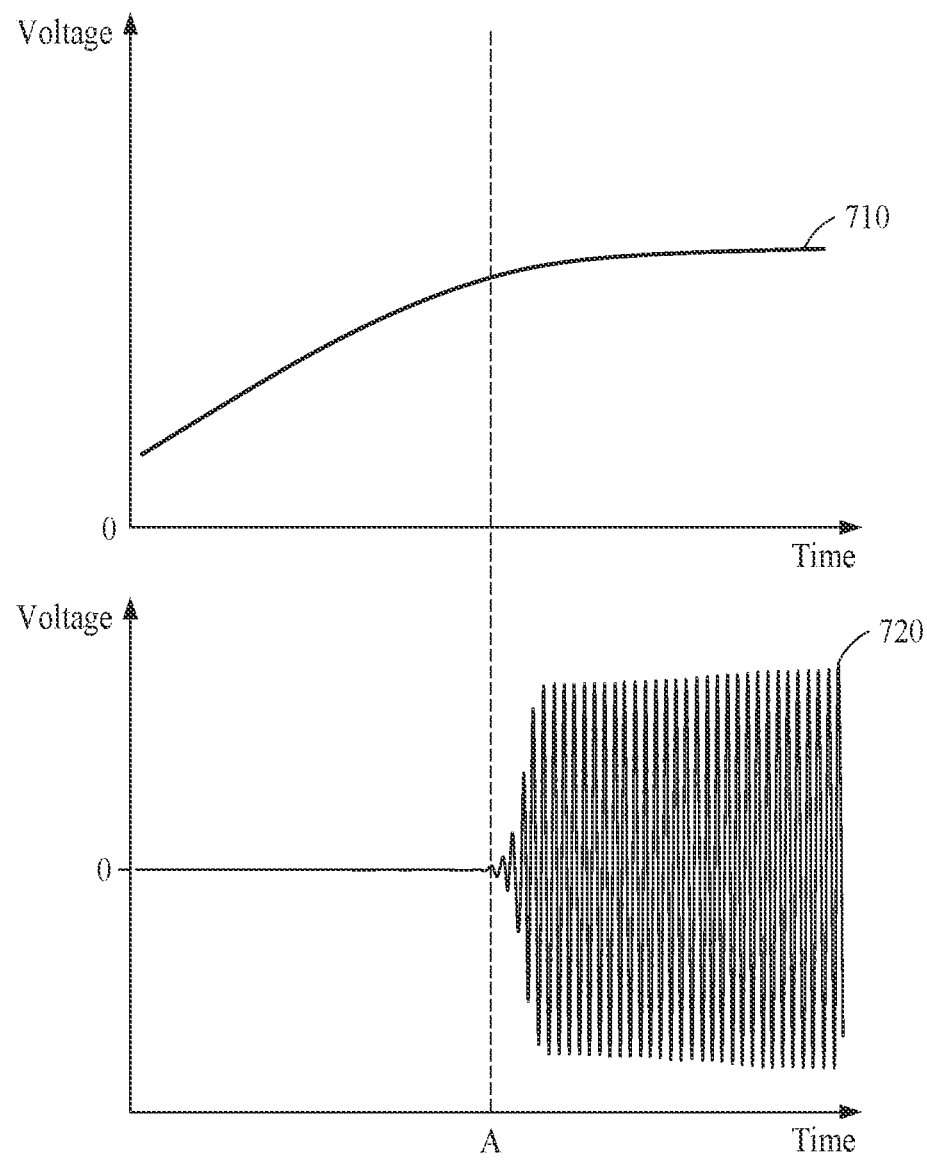
FIG. 7 illustrates an example of an operation of a power oscillator.

FIG. 7 illustrates an example of an operation of a power oscillator (for example, the power oscillator 550).

Referring to FIG. 7, reference numeral 710 represents a change in the DC voltage stored in the storage device 530 over time, and reference numeral 720 represents a change in a voltage signal output from the power oscillator 550 over time. Charges may start to accumulate in the storage device 530 by a current supplied from the rectifier 520 to the storage device 530, and a magnitude of the DC voltage may gradually increase over time as the current is supplied. When the DC voltage stored in the storage device 530 reaches (for example, is greater than or equal to) a predetermined reference value (for example, a threshold), the power oscillator 550 may start to oscillate. For example, when the magnitude of the DC voltage stored in the storage device 530 reaches the reference value at a point A in time, the power oscillator 550 may be automatically activated at the point A in time and start to oscillate by the structure of the circuit of FIG. 5. The power oscillator 550 may remain in an off state until the DC voltage stored in the storage device 530 reaches the reference value, may start to oscillate at the point A in time at which the DC voltage reaches the reference value, and may generate an AC power signal of a second frequency, without being controlled by a control signal. As described above, the wireless power relay apparatus 500 may not require a configuration to actively control the power oscillator 550 and may fully passively operate.

Figure 8:
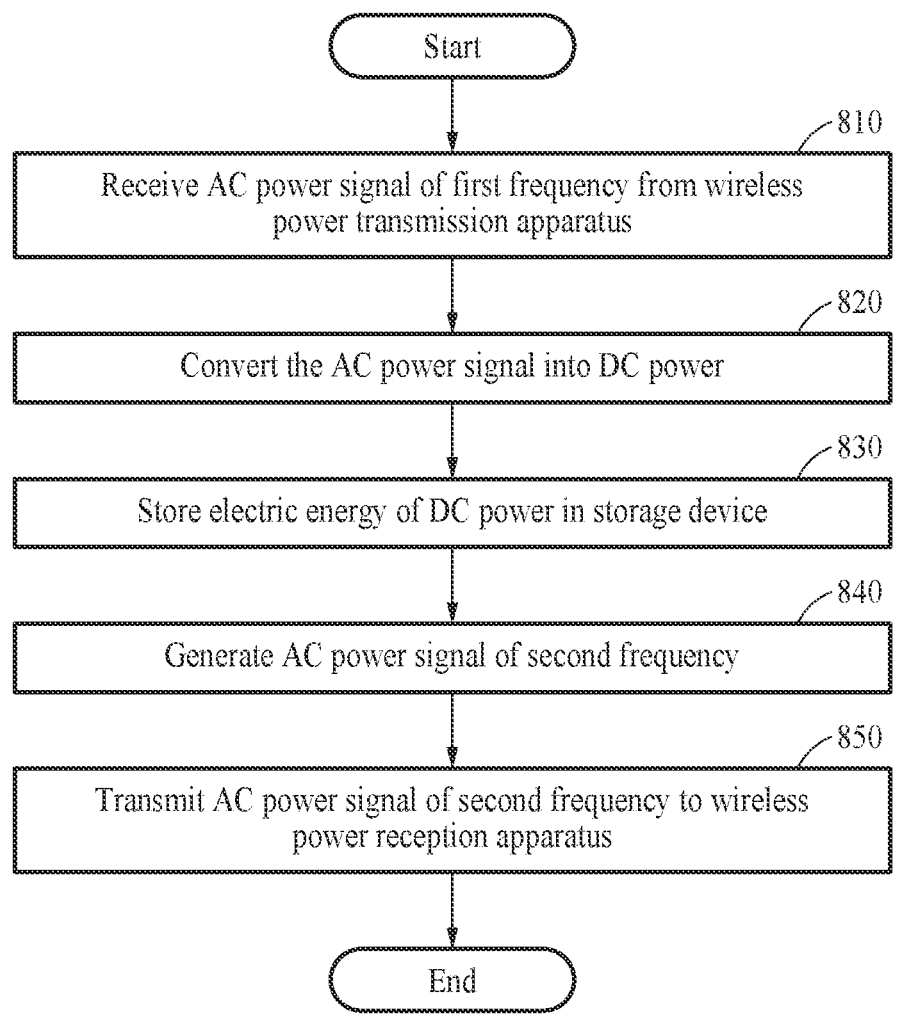
FIG. 8 illustrates an example of a wireless power relay method.

FIG. 8 illustrates an example of a wireless power relay method. The wireless power relay method may be performed by, for example, a wireless power relay apparatus described above (for example, the wireless power relay apparatus 120, 220, 320, 400, 500, and/or 620).

Referring to FIG. 8, in operation 810, the wireless power relay apparatus may receive, using a first antenna, an AC power signal of a first frequency from a wireless power transmission apparatus. The first antenna may be implemented as a coil, and may receive the AC power signal of the first frequency from the wireless power transmission apparatus through mutual coupling between coils.

In operation 820, the wireless power relay apparatus may convert, using a rectifier, the AC power signal of the first frequency into a DC power. By converting the AC power signal into the DC power, a DC voltage may be generated. In operation 830, the wireless power relay apparatus may store electric energy of the DC power output from the rectifier in a storage device, for example, a capacitor.

In operation 840, the wireless power relay apparatus may generate, using a power oscillator, an AC power signal of a second frequency based on an output current of the rectifier and electric energy of a DC voltage stored in the storage device. The second frequency may be different from the first frequency and may be identical to an operating frequency for a wireless power reception of a wireless power reception apparatus. For example, when a reception of the AC power signal of the first frequency is started and when the DC voltage stored in the storage device reaches a reference value, the power oscillator may start to oscillate to generate the AC power signal of the second frequency. In operation 850, the wireless power relay apparatus may transmit the AC power signal of the second frequency via a second antenna to the wireless power reception apparatus.

The wireless power transmission systems, wireless power transmission apparatuses, wireless power relay apparatuses, wireless power reception apparatuses, first antennas, rectifiers, storage devices, power oscillators, second antennas, second antennas, first insulating layers, circuit boards, second insulating layers, wireless power transmission system 100, wireless power transmission apparatus 110, wireless power relay apparatus 120, wireless power reception apparatus 130, wireless power transmission apparatus 210, wireless power relay apparatus 220, wireless power transmission apparatus 310, wireless power relay apparatus 320, wireless power reception apparatus 340, wireless power relay apparatus 400, first antenna 410, rectifier 420, storage device 430, power oscillator 440, second antenna 450, wireless power relay apparatus 500, first antenna 510, a rectifier 520, storage device 530, second antenna 540, power oscillator 550, wireless power transmission apparatus 610, wireless power relay apparatus 620, first antenna 630, first insulating layer 632, circuit board 634, second insulating layer 636, second antenna 638, apparatuses, units, modules, devices, and other components described herein with respect to FIGS. 1-8 are implemented by or representative of hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-8 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions used herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

What is claimed is:

1. A wireless power relay apparatus comprising:
   a first antenna configured to wirelessly receive an alternating current (AC) power signal of a first frequency from a wireless power transmission apparatus;
   a rectifier configured to convert the received AC power signal into a direct current (DC) power;
   a storage device configured to store electric energy of the DC power output from the rectifier;
   a power oscillator configured to generate an AC power signal of a second frequency in response to receiving an output current of the rectifier and a DC voltage stored in the storage device reaching a reference value; and
   a second antenna configured to transmit the AC power signal of the second frequency to a wireless power reception apparatus.

2. The apparatus of claim 1, wherein the power oscillator is configured to start to oscillate, in response to the first antenna starting to receive the AC power signal of the first frequency and the DC voltage stored in the storage device reaching the reference value.

3. The apparatus of claim 2, wherein the power oscillator is configured to remain in an off state until the DC voltage reaches the reference value, start to oscillate at a point in time at which the DC voltage reaches the reference value, and generate the AC power signal of the second frequency, without being controlled by a control signal.

4. The apparatus of claim 1, wherein the power oscillator is configured to oscillate at the second frequency based on the DC voltage supplied from the storage device and the current supplied from the rectifier.

5. The apparatus of claim 1, wherein the rectifier, the storage device, and the second antenna are connected to a common node.

6. The apparatus of claim 1, wherein
   the storage device is a capacitor, and
   an end of the capacitor is connected to a ground terminal, and another end of the capacitor is connected to the rectifier and the second antenna.

7. The apparatus of claim 1, wherein the wireless power relay apparatus is configured to be detachably mounted on a surface of the wireless power transmission apparatus.

8. The apparatus of claim 7, wherein the first antenna is configured to wirelessly receive the AC power signal of the first frequency from the wireless power transmission apparatus when the wireless power relay apparatus is detachably mounted on the surface of the wireless power transmission apparatus.

9. The apparatus of claim 1, wherein
   the wireless power transmission apparatus is a mobile electronic device, and
   the AC power signal of the first frequency is generated from electric energy stored in a battery of the mobile electronic device.

10. The apparatus of claim 1, wherein the wireless power reception apparatus is an implantable apparatus or a body attachment apparatus.

11. The apparatus of claim 1, wherein the second frequency is different from the first frequency, and the second frequency is equal to an operating frequency for a wireless power reception of the wireless power reception apparatus.

12. The apparatus of claim 1, wherein
the rectifier comprises a plurality of diodes, and
the power oscillator comprises two transistors and a capacitor connected to an end of each of the two transistors.

13. A wireless power transmission system comprising:
a wireless power transmission apparatus configured to wirelessly transmit an alternating current (AC) power signal of a first frequency; and
a wireless power relay apparatus configured to
receive the AC power signal of the first frequency,
convert the received AC power signal into a direct current (DC) power,
generate an AC power signal of a second frequency in response to a DC voltage of stored electrical energy of the DC power reaching a reference value, and
transmit the generated AC power signal of the second frequency to a wireless power reception apparatus.

14. The system of claim 13, wherein the wireless power relay apparatus comprises:
a rectifier configured to convert the received AC power signal into the DC power;
a storage device configured to store the electric energy of the DC power output from the rectifier; and
a power oscillator configured to generate the AC power signal of the second frequency based on an output current of the rectifier and electric energy of a DC voltage stored in the storage device.

15. The system of claim 13, wherein the wireless power relay apparatus is configured to be detachably mounted on a surface of the wireless power transmission apparatus.

16. The system of claim 13, wherein
the wireless power transmission apparatus is a mobile electronic device, and
the wireless power reception apparatus is an implantable apparatus or a body attachment apparatus.

17. A wireless power relay method comprising:
wirelessly receiving, using a first antenna, an alternating current (AC) power signal of a first frequency from a wireless power transmission apparatus;
converting, using a rectifier, the received AC power signal into a direct current (DC) power;
storing, in a storage device, electric energy of the DC power output from the rectifier;
generating, using a power oscillator, an AC power signal of a second frequency in response to receiving an output current of the rectifier and a DC voltage stored in the storage device reaching a reference value; and
transmitting, using a second antenna, the AC power signal of the second frequency to a wireless power reception apparatus.

18. The method of claim 17, wherein the generating of the AC power signal of the second frequency comprises the power oscillator starting to oscillate, in response to the first antenna starting to receive the AC power signal of the first frequency and the DC voltage reaching the reference value.

19. The method of claim 17, wherein
the wireless power transmission apparatus is a mobile electronic device,
the AC power signal of the first frequency is generated from electric energy stored in a battery of the mobile electronic device, and
the wireless power reception apparatus is an implantable apparatus or a body attachment apparatus.

20. The method of claim 17, wherein the second frequency is different from the first frequency and is identical to an operating frequency for a wireless power reception of the wireless power reception apparatus.

\* \* \* \* \*